United States Patent [19]

Behler et al.

[11] Patent Number: 4,996,364

[45] Date of Patent: Feb. 26, 1991

[54] USE OF ALKALINE EARTH SALTS OF POLYCARBOXYLIC ACID MONOESTERS AS ALKOXYLATION CATALYSTS

[75] Inventors: Ansgar Behler, Bottrop; Uwe Ploog, Haan, both of Fed. Rep. of Germany

[73] Assignee: Henkel Kommanditgesellschaft auf Aktien, Duesseldorf, Fed. Rep. of Germany

[21] Appl. No.: 336,157

[22] Filed: Apr. 11, 1989

[30] Foreign Application Priority Data

Apr. 12, 1988 [DE] Fed. Rep. of Germany ....... 3812168

[51] Int. Cl.$^5$ ............................................. C07C 213/00
[52] U.S. Cl. .................................... 564/475; 564/505; 568/618; 568/679
[58] Field of Search ................ 564/475, 505; 568/679, 568/618

[56] References Cited

FOREIGN PATENT DOCUMENTS 0082569  6/1983  European Pat. Off. .
 085167  8/1983  European Pat. Off. .
0091146 10/1983  European Pat. Off. .
0092256 10/1983  European Pat. Off. .
0115083  8/1984  European Pat. Off. .

OTHER PUBLICATIONS

Wharry et al., JAOCS, vol. 63, pp. 691-695 (1986).

Dillan et al., HAPPI, May 1986, pp. 52-54.

*Primary Examiner*—Richard L. Raymond
*Assistant Examiner*—Scott C. Rand
*Attorney, Agent, or Firm*—Ernest G. Szoke; Wayne C. Jaeschke; Real J. Grandmaison

[57] ABSTRACT

Alkaline earth salts of polycarboxylic acid monoesters corresponding to general formula I $$[R\text{-}(OC_mH_{2m})_n\text{-}O\text{-}CO\text{-}A(COO^-)_o]_p M^{2+} \quad (I)$$

in which
R is a radical selected from the group consisting of a linear or branched $C_1$–$C_{22}$ alkyl or $C_3$–$C_{22}$ alkenyl, phenyl, alkylphenyl containing 1 to 3 $C_1$–$C_{15}$ alkyl groups, benzyl and phenethyl,
A is a saturated or unsaturated, acyclic or cyclic $C_2$–$C_6$ hydrocarbon radical with two or three bonds or a benzene group with two or three bonds,
M is an alkaline earth metal selected from the group consisting of Ca, Ba and Sr;
m is the number 2 or 3;
n is a number from 1 to 20;
o is the number 1 and p is the number 2 or o is the number 2 and p is the number 1, are employed as catalysts for the ethoxylation or propoxylation of compounds containing active hydrogen atoms.

8 Claims, No Drawings

USE OF ALKALINE EARTH SALTS OF POLYCARBOXYLIC ACID MONOESTERS AS ALKOXYLATION CATALYSTS

BACKGROUND OF THE INVENTION

1. Field of the Invention.

This invention relates to the use of alkaline earth salts of polycarboxylic acid monoesters as a catalyst for the ethoxylation or propoxylation of compounds containing active hydrogen atoms.

2. Discussion of Related Art.

Various catalysts have been used for the aforementioned polyalkoxylation reaction; for example, calcium and strontium hydroxides, alkoxides and phenoxides (EP-A No. 00 92 256), calcium alkoxides (EP-A No. 00 91 146), barium hydroxide (EP-B No. 0 115 083), basic magnesium compounds, for example alkoxides (EP-A No. 00 82 569), magnesium and calcium fatty acid salts (EP-A No. 0 85 167).

The catalysts mentioned above are attended, inter alia, by the disadvantage that they are difficult to incorporate in the reaction system and/or are difficult to produce.

Other typical polyalkoxylation catalysts are potassium hydroxide and sodium methylate.

A narrow range of the degree of polyalkoxylation is of particular importance for fatty alcohol polyalkoxylates, cf. JAOCS, Vol. 63, 691-695 (1986), and HAPPI, 52 -54 (1986). Accordingly, the so-called "narrow-range" alkoxylates have above all the following advantages:

low pour points,
relatively high smoke points,
fewer mols alkoxide to achieve solubility in water,
fewer hydrotropes for introduction into liquid universal detergents,
relatively faint odor through the presence of free (unreacted) fatty alcohols, and
reduced pluming in the spray-drying of detergent slurries containing fatty alcohol polyalkoxylate surfactants.

The range or rather homolog distribution of fatty alcohol polyalkoxylates depends mainly on the type of catalyst used. A measure of the homolog distribution is the so-called Q value according to the following relation:

$$Q = n^* p^2$$

in which $n^*$ is the average number of adducts (average degree of ethoxylation) and p is the percentage of the adduct having a certain EO degree which is predominantly formed. Accordingly, a high Q value signifies a narrow homolog distribution range.

DESCRIPTION OF THE INVENTION

Other than in the operating examples, or where otherwise indicated, all numbers expressing quantities of ingredients or reaction conditions used herein are to be understood as modified in all instances by the term "about".

It has now been found that polyethoxylated or polypropoxylated fatty alcohols having a high Q value can be obtained using the alkaline earth salts of polycarboxylic acid monoesters corresponding to the following general formula I in accordance with the invention. The alkaline earth salts to be used in accordance with the invention have the advantage over the known catalysts in that they provide for short reaction times and are soluble in the reaction system in contrast, for example, to the alkaline earth salts according to the prior art.

The alkaline earth salts of polycarboxylic acid monoesters in accordance with this invention correspond to general formula I $$[R-(OC_mH_{2m})_n-O-CO-A(COO^-)_o]_p M^{2+} \quad (I)$$

in which
R is a radical selected from the group consisting of a linear or branched $C_1$-$C_{22}$ alkyl or $C_3$-$C_{22}$ alkenyl, phenyl, alkylphenyl containing 1 to 3 $C_1$-$C_{15}$ alkyl groups, benzyl and phenethyl,
A is a saturated or unsaturated, acyclic or cyclic $C_2$-$C_6$ hydrocarbon radical with two or three bonds or a benzene group with two or three bonds,
M is an alkaline earth metal selected from the group consisting of Ca, Ba and Sr;
m is the number 2 or 3,
n is a number from 1 to 20; and
o is the number 1 and p is the number 2, or o is the number 2 and p is the number 1.

The polycarboxylic acid monoesters on which the alkaline earth salts to be used in accordance with the invention are based are known and, in some cases, commercially obtainable compounds. They may be obtained by reaction of the corresponding anhydrides with alcohols corresponding to the formula R—OH or alkoxylated alcohols corresponding to the formula R—$(OC_mH_{2m})_n$—OH, in which R is as defined above, and preparation of the corresponding alkaline earth salts from the resulting polycarboxylic acid monoester with basic Ca, Ba and Sr compounds, particularly the oxides, hydroxides and carbonates. The polycarboxylic acid monoesters may also be obtained from the free polycarboxylic acids by reaction with the alcohols or alkoxylated alcohols mentioned in the stoichiometric quantities corresponding to the monoester.

In the context of the invention, compounds containing active hydrogen atoms are understood to be, for example, fatty alcohols, fatty amines and amines which, on ethoxylation or propoxylation, form nonionic surfactants. A typical example of this is the reaction of fatty alcohols normally containing 10 to 18 carbon atoms with ethylene oxide and/or propylene oxide in the presence of a catalyst, the fatty alcohols reacting with several molecules of ethylene oxide and/or propylene oxide.

In another advantageous embodiment of the invention, the structural element $$O-CO-A(COO^-)_o$$

of the polycarboxylic acid monoesters corresponding to general formula I is a polycarboxylic acid residue selected from the group consisting of maleic, succinic, glutaric, phthalic, dihydrophthalic, tetrahydrophthalic, hexahydrophthalic and trimellitic acid. The polycarboxylic acids mentioned above form cyclic anhydrides which can be converted with the alcohols or alkoxylated alcohols in molar ratios of 1:1 into the corresponding polycarboxylic acid monoesters.

In another advantageous embodiment of the invention, the alkaline earth salt of the polycarboxylic acid monoesters corresponding to general formula I is an alkaline earth salt of a maleic acid semiester corresponding to general formula II $$[R-(OC_mH_{2m})_n-O-CO-CH=CH-COO^-]_2 \; M^{2+} \quad (II)$$

in which R, M, m and n are as defined above.

One advantageous embodiment of the invention comprises using alkaline earth salts of polycarboxylic acid monoesters corresponding to general formula I or II, in which R is a radical selected from the group consisting of linear or branched $C_1$-$C_8$ alkyl, and m, n and M are as defined above because these compounds are soluble in methanol. The more highly alkylated derivatives are only soluble in alcohols higher than methanol, although they may also readily be used as alkoxylation catalysts in the context of the invention.

Another preferred embodiment of the invention comprises using alkaline earth salts of polycarboxylic acid monoesters corresponding to general formula I or II, in which n is a number of 1 to 12. Compounds in which n is greater than 20 are less preferred because their catalytic activity is less than optimal.

According to the invention, the alkaline earth salts of polycarboxylic acid monoesters corresponding to general formula I or II are used as a catalyst in a quantity of 0.1 to 2% by weight, based on the end product of the ethoxylation or propoxylation reaction.

In the alkaline earth salts of general formula I or II to be used in accordance with the invention, the radical R may be, for example, a linear or branched alkyl radical such as methyl, ethyl, propyl, n-butyl, i-butyl, pentyl or hexyl, and also a fatty alkyl radical such as capryl, capric, lauryl, myristyl, cetyl, palmitoleyl, oleyl, stearoyl, gadoleyl, erucyl or behenyl. Where R is a fatty alkyl radical, mixtures of these radicals as formed, for example, in the reaction of polycarboxylic anhydrides with technical grade fatty alcohols, may be present.

The alkaline earth salts to be used in accordance with the invention are liquid to wax-like, and are soluble or readily incorporable in the compounds to be alkoxylated.

The invention is illustrated by the following Examples.

A. General procedure for the preparation of alkaline earth salts of polycarboxylic acid monoesters to be used in accordance with the invention:

The polycarboxylic acid monoesters were dissolved or suspended in a mixture of water, ethanol and isopropanol (3:2:1) and reacted at 90° C with equimolar quantities of alkaline earth metal acetate. The quantity of alkaline earth metal acetate added was calculated from the acid value of the monoester. The acetic acid liberated was distilled off with the solvent.

The catalysts of general formula II listed in Table I were prepared.

B. Ethoxylation of lauryl alcohol with 6 mol of ethylene oxide with the catalysts to be used in accordance with the invention:

The catalyst was dissolved in the lauryl alcohol. The solution was transferred to an autoclave suitable for the alkoxylation. The autoclave was purged with nitrogen and evacuated for 30 minutes at a temperature of 100° C. The temperature was then increased to 180° C. and the required quantity of ethylene oxide introduced at a pressure of 4 to 5 bar. On completion of the reaction, the reaction mixture was left reacting for 30 minutes.

The results obtained in this way in the above ethoxylation with the catalysts to be used in accordance with the invention are shown in Table II where;
Q = the Q value defined above,
OH value, actual/required = OH values of the polyethoxylated lauryl alcohols obtained as end product,
Cat-% = catalyst concentration, based on the end product,
t = reaction time of the polyethoxylation in hours.

The results obtained with the catalysts of formula II are shown in Table II. For comparison purposes, Table II also includes a test using a known alkoxylation catalyst, i.e., sodium methylate.

The comparison shows that the catalysts to be used in accordance with the invention give higher Q values, i.e. a better homolog distribution, than sodium methylate.

TABLE I

| Catalysts of general formula II produced | | | |
|---|---|---|---|
| Catalyst no. | R | n | M |
| 1 | $C_8$ alkyl | 4 | Ca |
| 2 | $C_2$ alkyl | 2 | Ca |
| 3 | $C_2$ alkyl | 2 | Ba |
| 4 | $C_{12}$ alkyl | 6 | Sr |
| 5 | $C_{18'}/C_{18}$ alky;* | 0 | Sr |

*technical grade oleyl/stearyl semiester

TABLE II

| Ethoxylation of a commercial lauryl alcohol | | | | | |
|---|---|---|---|---|---|
| Catalyst | | t | | OH value | |
| no. | Cat-% | (h) | Q | actual | required |
| 1 | 0.5 | 7.5 | 1314 | 128 | 128 |
| 2 | 0.5 | 12 | 1221 | 131.9 | 122.2 |
| 3 | 0.5 | 3 | 1159 | 125.8 | 124.7 |
| 4 | 0.5 | 6.5 | 1368 | 126.3 | 126.3 |
| 5 | 0.5 | 3 | 1147 | 129.4 | 124.7 |
| $NaOCH_3$ | 0.5 | 4 | 595 | 128.8 | 126.8 |

We claim:

1. The process of ethoxylating or propoxylating a compound containing an active hydrogen atom, said compound being selected from a fatty alcohol, fatty amine, and an amine which on ethoxylation or propoxylation forms a nonionic surfactant, comprising contacting said compound with an alkaline earth salt of a polycarboxylic acid monoester corresponding to general formula I $$[R-(OC_mH_{2m})_n-O-CO-A(COO^-)_o]_p \; M^{2+} \quad (I)$$

in which
R is a radical selected from the group consisting of a linear or branched $C_1$-$C_{22}$ alkyl or $C_3$-$C_{22}$ alkenyl, phenyl, alkylphenyl containing to 3 $C_1$-$C_{15}$ alkyl groups, benzyl and phenethyl,
A is a saturated or unsaturated, acyclic or cyclic $C_2$-$C_6$ hydrocarbon radical with two or three bonds or a benzene group with two or three bonds,
M is an alkaline earth metal selected from the group consisting of Ca, Ba and Sr;
m is the number 2 or 3;
n is a number from about 1 to about 20;
o is the number 1 and p is the number 2, or o is the number 2 and p is the number 1.

2. The process in accordance with claim 1 wherein the structural element $$-O-CO-A(COO^-)_o$$

of the polycarboxylic acid monoester corresponding to general formula I is a polycarboxylic acid residue selected from the group consisting of maleic, succinic, glutaric, phthalic, dihydrophthalic, tetrahydrophthalic, hexahydrophthalic and trimellitic acid.

3. The process in accordance with claim 1 wherein said polycarboxylic acid monoester corresponding to general formula I comprises an alkaline earth salt of a maleic acid semiester corresponding to general formula II $$[R-(OC_mH_{2m})_n-CO-CH=CH-COO^-]_2 M^{2+} \quad (II)$$

in which R, M, m and n are as defined in claim 1.

4. The process in accordance with claim 1 wherein R is a radical selected from the group consisting of a linear or branched $C_1$-$C_8$ alkyl group.

5. The process in accordance with claim 1 wherein n is a number from about 1 to about 12.

6. The process in accordance with claim 1 wherein said polycarboxylic acid monoester is present in an amount of from about 0.1 to about 2% by weight, based on the weight of the alkoxylation product.

7. The process in accordance with claim 1 wherein the ethoxylating or propoxylating step is conducted with ethylene oxide or propylene oxide.

8. The process in accordance with claim 1 wherein said polycarboxylic acid monoester is an alkoxylation catalyst.

* * * * *

UNITED STATES PATENT AND TRADEMARK OFFICE
CERTIFICATE OF CORRECTION

PATENT NO. : 4,996,364
DATED : February 26, 1991
INVENTOR(S) : Behler et al.

It is certified that error appears in the above-identified patent and that said Letters Patent is hereby corrected as shown below:

In Claim 3, Column 5, line 14 should read $$--[R-(OC_mH_{2m})_n-O-CO-CH=CH\text{---}COO^-]_2M^{2+}--$$

Signed and Sealed this

Twenty-eighth Day of July, 1992

*Attest:*

DOUGLAS B. COMER

*Attesting Officer*   Acting Commissioner of Patents and Trademarks